United States Patent [19]

Doyle

[11] Patent Number: Plant 6,759

[45] Date of Patent: Apr. 25, 1989

[54] PEACH TREE, "FLAVOR QUEEN"

[76] Inventor: James F. Doyle, 7685 N. Thompson Ave., Clovis, Calif. 93612

[21] Appl. No.: 138,922

[22] Filed: Dec. 28, 1987

[51] Int. Cl.[4] ..... A01H 5/03

[52] U.S. Cl. ..... Plt./43

[58] Field of Search ..... Plt./43

*Primary Examiner*—Robert E. Bagwill

*Attorney, Agent, or Firm*—Worrel & Worrel

[57] ABSTRACT

A new and distinct variety of Peach tree which is somewhat remotely similar to the Gemfree Peach Tree (U.S. Plant Pat. No. 1,409) with which it is most closely related in its date of harvest, but from which it is distinguished therefrom by producing fruit which are mature for commercial harvesting and shipment approximately June 4 through June 10 and which further produces a medium sized, globose shaped fruit having a semi-clingstone nature and which exhibits a deep red to a lighter orange-red skin color, a golden yellow colored flesh and has an excellent flavor.

1 Drawing Sheet

BACKGROUND OF THE NEW VARIETY

The present invention relates to a new and distinct variety of peach tree which has been denominated varietally as "Flavor Queen" and more particularly to such a peach tree which produces fruit that is mature for commercial harvesting and shipment approximately June 4 to June 10 and which is further distinguished as to novelty by producing a semi-clingstone fruit, the flesh of which is firm, crisp, and has a golden yellow color, and which further has a nearly globose shape, the fruit of the subject variety being rich in flavor and noticeably aromatic.

It has long been known that the purchase of fruits such as peaches, by consumers, is largely influenced by the fruit's exterior appearance, that is the fruit's size, shape, and exterior coloration. Thus, it has been recognized that it is desirable to provide a peach tree bearing fruit ripe for commercial harvesting in early June having the commercially aesthetic appeal such as that presented by the Flavor Queen Peach Tree. The fruit of the subject variety is noteworthy in that it produces fruit which have a highly attractive skin color of deep red (7-L-10) which lightens to an orange-red (3-J-11); and a superior globose shape.

ORIGIN AND ASEXUAL REPRODUCTION OF THE NEW VARIETY

The present variety of peach tree is the apparent product of a successful cross-pollination of either a Redtop Peach Tree (unpatented), or a Regina Peach Tree (unpatented), with the pollen extracted from a Snowflame Peach Tree (U.S. Plant Pat. No. 5,251). The cross-pollination procedure was performed by the applicant in 1978, at the applicant's orchard which is located at 7685 North Thompson Ave., Clovis, Calif., as part of an ongoing variety development program. The cross-pollination was performed by placing Snowflame Peach Tree (U.S. Plant Pat. No. 5,251) pollen on emasculated flowers growing on a tree grafted with limbs of both the Redtop Peach Tree (unpatented) and the Regina Peach Tree (unpatented). Following this cross-pollination, seeds were produced and were planted in the spring of 1979 at the above-identified orchard. The applicant first noted the desirable characteristics of the subject tree in 1982. After appreciating the excellent qualities of the subject variety, the applicant asexually reproduced the instant variety by grafting it into peach rootstocks in order to hasten the evaluation process. Fruit was borne on the grafted trees in 1984 and it has subsequently been determined that the first asexual reproduction dependably and accurately reproduced the superior characteristics observed by the applicant in the original seedling.

SUMMARY OF THE NEW VARIETY

The Flavor Queen Peach Tree is characterized as to novelty by producing a high quality early season fruit having an appealing shape and a highly attractive skin color. The fruit of the Flavor Queen Peach Tree is ripe for commercial harvesting and shipment from approximately June 4 to June 10 in the San Joaquin Valley of Central California; and is most closely similar to the Gemfree Peach Tree (U.S. Plant Pat. No. 1,409) which matures at approximately the same time but is distinguishable therefrom by producing fruit which have a superior color and shape. The fruit produced by the Gemfree Peach Tree (U.S. Plant Pat. No. 1,409) typically displays a greenish ground color when commercially ripe, and has a substantially elongated shape with a substantial tip. The Flavor Queen Peach Tree in contrast, produces fruit having an overall red blush and a bright yellow ground color. Moreover, the fruit of the instant variety displays a superior globose shape and no tip is evident. The above-identified characteristics in addition to the excellent flavor and aroma produced by the fruit of the Flavor Queen Peach Tree clearly indicates that this variety is a substantial improvement over those varieties which are commercially mature for harvesting and shipment at approximately the same harvesting period.

BRIEF DESCRIPTION OF THE DRAWINGS

The drawing is a color photograph of four mature fruit characteristic of the subject variety. Three of the fruit display skin colorations typical of fruit which are sufficiently matured for commercial harvesting and shipment. Another fruit has been cross sectioned in a plane which is substantially parallel to the axial plane thereby displaying the flesh coloration of a typical mature fruit. The drawing also shows a typical twig bearing characteristic leaves which display the ventral and dorsal coloration thereof, together with a typical stone, all of the instant variety.

DETAILED DESCRIPTION

Referring more specifically to the pomological details of this new and distinct variety of peach tree, the following characteristics were observed under the ecological conditions prevailing at the orchard of origin which is located in Clovis, County of Fresno, Calif. All major color code designations are by reference to the Dictionary of Color, by Maerz and Paul, published in 1950.

TREE

Size: Average.

Form: Upright and spreading with form and density determined by pruning practices.

Vigor: Average; hardy when grown under typical San Joaquin Valley climatic conditions.

Productivity: Productive.

Trunk:

*Generally.*—The trunk is of medium diameter and surface texture and having abundant, relatively large lenticels. Brown colored (7-A-10), cork-like tissue surrounds the lenticel openings.

*Bark color.*—Grey-brown, (8-E-9); abundant scarf skin is evident.

Branches: Mature branches display a normal peach tree surface texture and have a diameter which is slightly less than average. The lenticels are moderate in number, small, light colored and raised in appearance. The color of the mature branches varies from brown-green, (13-H-8), to a dark brown, (8-H-10). Immature branches display a light green color, (17H-5), with some red tinge over exposed surfaces.

Leaves:

*Size.*—Generally — medium.

*Average length.*—Approximately 150 mm.

*Average width.*—Approximately 37 mm.

*Form.*—Generally — narrowly lanceolate with an acuminate apex.

*Marginal form.*—Uniform; crenate; the crenations are, however, quite shallow; moderately undulate.

*Color — dorsal surface.*—Dark green, (23-L-6).

*Color — ventral surfaces.*—Light grey-green, (21-E-4).

*color — lower mid-vein.*—Light green-yellow, (18-H-3).

*Petiole.*—Average length — approximately 9 to 11 mm.; average thickness — approximately 1.5 mm.; color — light green, )19-I-3).

(i Leaf glands — size.—Average.

*Leaf glands — form.*—Predominately Reniform.

*Leaf glands — color.*—Light green (17-J-3) and shiny when young, darkening and deteriorating with avancing maturity.

*Leaf glands — numbers.*—Variable, from 3 to 6.

*Leaf glands — position.*—Most of the glands (1–3) are positioned along the lowermost basal portion of the leaf margin, with any remaining glands positoned higher on the basal leaf margin.

*Stipules — generally.*—Two stipules are usually present, and subtend the leaf petiole.

*Stipules — color.*—Light green when young, (17-H-4), some red tinge is evident.

*Early deciduous.*—Yes.

Flower buds and scale:

*Size.*—Generally — medium.

*Form.*—Conic.

*Numbers of buds.*—Most commonly one to two buds per node were observed.

*Surface texture.*—Generally — pubescent.

*Color.*—Scales — grey-brown (7-C-8).

Flowers:

*Date of full bloom.*—March 12 at Clovis, Calif. The date of bloom is average as compared with other known varieties.

*Size.*—Generally — small.

*Diameter.*—Approximately 26 to 29 mm. when fully expanded.

*Flower type.*—Non-showy. The flowers of the subject variety are one of the larger of this particular blossom form.

*Bloom amount.*—Average in density for the species.

*Petals — size.*—Small; shape — oval to obovate with a short substantially truncate claw; length — approximately 14 to 16 mm.; width — approximately 10 to 11 mm.; color — light pink (1-F-2), in the central petal area with a darker pink rose color (1-E-4) along the margin; the petal lightens in color with advancing maturity. The petals display a tendency to roll strongly inward along the longitudinal axis. Color — Basal areas — The petals and the claw darken to a deep rose color (1-H-5), with advancing maturity.

*Petals — marginal form.*—Moderately undulate; petal apices are wavy.

*Pedicel — size.*—Average.

*Pedicel — length.*—Approximately 3 mm.

*Pedicel — thickness.*—Approximately 1.5 mm.

*Pedicel — color.*—Bright green (17-(-4).

*Nectaries.*—Color — dark orange (11-G-11), this color darkens and becomes dull with advancing maturity.

*Anthers.*—Size — medium; color — dorsal surfaces — red, (4-JH-11); Color — ventral surface — buff, (9-G-3).

*Stamens — length.*—Approximately 15 to 17 mm., the stamens are usually slightly longer than the pistil.

*Stamens — color.*—Variable, nearly white to light pink, (1-C-1) when young; this color darkens with advancing maturity to a rose-violet, (1-H-5).

*Pistil.*—Length — approximately 10 to 14 mm.; texture-pubescent; color — light yellow-green (17-D-2).

*Pollen production.*—Abundant.

*Pollen.*—Color — Yellow, (10-L-3).

FRUIT

Maturity when described: Ripe for commercial harvesting and shipment, approximately June 4 through June 10 in Clovis, Calif.

Size:

*Generally.*—Medium and uniform.

*Average cheek diameter.*—Approximately 61 mm.

*Average suture diameter.*—Approximately 61 mm.

*Average axial diameter.*—Approximately 58 mm.

Form: Uniform, and very regular; typically asymmetrical; globose to very slightly ovate in its lateral aspect, uniformly globose apically and basally.

Suture: The suture is generally a distinct but narrow line approximately 1 to 1.5 mm. wide. The suture is usually flat but may be very slightly depressed, becoming deeper basally with occasional folding over the basal shoulder. The suture color is variable inasmuch as the suture usually takes on the same coloration as the underlying blush or ground color in the vicinity of the suture. On some fruit, portions of the suture may be pigmented, usually with a dark purple-red color (6-L-9). From time to time fine stitching appears along the suture line, this appears most frequently over the apical shoulder, although occasionally it appears from the base to the apex. The pistil point is variable from perfectly apical to fully oblique. A slight depression appears on the dorsal suture side at the apex just beyond the pistil point.

Ventral surface:

*Generally.*—Rounded with occasional lipping sometimes evident on one side.

Stem cavity:

*Generally.*—Wide, although moderately shallow.

*Stem cavity width.*—Approximately 18 to 21 mm. wide.

*Stem cavity length.*—Approximately 22 to 24 mm.

*Stem cavity depth.*—Approximately 8 to 10 mm. The ventral suture is typically clearly visible in the stem cavity. From time to time it may appear moderately folded along the suture line.

Base:

*Position.*—Very slightly oblique to the fruit axis and generally shorter on the ventral suture side.

Apex:

*Shape.*—Rounded; slight depressions appear on both the ventral suture side of the apex and the dorsal suture side of the apex. The pistil point varies from apical to oblique.

Stem:

*Size.*—Average; length — approximately 6 to 8 mm.; thickness — approximately 2.5 to 3.0 mm.

*Color.*—A light green-yellow, (17-J-4); the stem may occasionally be tinged with red.

Skin: Moderately pubescent; tenacious to flesh at commercial maturity. No observed tendency to crack or split; average in thickness; and mild flavored.

Skin color:

*Generally.*—The subject variety displays a red blush color which covers approximately 60% to 80% of the fruit surface. The blush pattern exhibits moderate streaking. This is most strongly so apically. There is substantial mottling, and numerous light colored dots appear over the apical shoulders. Basally there is less streaking with broad contrasting areas of solid red blush and yellow ground color. The ground color is bright yellow (10-J-5). The blush color is variable although typically it is a deep red (7-L-10) lightening to an orange-red (3-J-11) in between the darker streaks.

Flesh color:

*Generally.*—A golden yellow (9-K-6), which extends from skin to the pit cavity with no red coloration evident in the flesh at commercial maturity. Some light red flecking may develop with advancing maturity.

Flesh texture:

*Commercial maturity.*—The flesh of the subject variety is firm and crisp, however, the flesh softens and becomes juicy with advancing maturity.

Flesh fibers:

*Numbers.*—Plentiful, especially in the pit cavity.

*Texture.*—Medium and tender.

Ripening: Even. p0 Flavor: Rich, and mildly acidic.

Aroma: Yes, above average.

Eating quality: Very good.

Stone:

*Attachment.*—Semi-clingstone. The stone of the subject variety is moderately tight at commercial maturity but breaks free with less effort as the fruit ages, and approaches tree ripe.

*Size.*—Generally — small to medium; length — approximately 35 mm.; width — approximately 25 mm.; thickness — approximately 18 mm.

*Form.*—Variable, oval to slightly obovate.

*Base.*—Rounded and occasionally slightly truncate.

*Hilum.*—Shape — narrowly oval; moderately eroded.

*Apex.*—Shape — rounded with a sharp acuminate tip.

*Sides.*—Texture — a generally coarse surface texture laterally with abundant pits, grooves and ridges; deep grooves appear over the apical shoulder laterally; fine grooves are evident over the basal shoulder and converge basally.

*Ventral surface.*—Generally — moderately narrow with a prominent wing evident in the basal suture area. The wings are less conspicuous in the vicinity of mid-suture and towards the apex.

*Dorsal surface.*—Texture — coarse; a moderately deep groove runs from the base to mid-suture and is subtended by coarse ridges. The dorsal suture is heavily eroded and is occasionally concave in form. This is most apparent from the apex to slightly above the mid-suture area.

*Color.*—Dry — light tan, (9-J-4).

*Tendency to split.*—Not observed.

Keeping quality: Good.

Shipping quality: The subject variety has not yet been shipped in volume, however, the firm and crisp flesh texture at commercial maturity strongly indicates that the variety will have noteworthy shipping qualities.

Fruit use: Fresh market for use in both local and long distance markets.

Although the new variety of peach tree possesses the described characteristics noted above as a result of the growing conditions prevailing in Fresno County, Calif., in the central San Joaquin Valley, it is to be understood that variations of the usual magnitude and characteristics incident to the changes in growing conditions, fertilization, pruning and pest control are to be expected.

Having thus described and illustrated my new variety of peach tree, what I claim as new and desire to secure by Plant Letters Patent is:

1. A new and distinct variety of peach tree substantially as illustrated and described which is somewhat remotely similar to the Gemfree Peach Tree (U.S. Plant Pat. No. 1,409) which matures in approximately the same season but from which it is distinguished therefrom and characterized as to novelty by producing fruit which are mature for commercial harvesting approximately June 4 through June 10 in the San Joaquin Valley of central California and which additionally produces medium sized, globose shaped fruit which have a semi-clingstone nature, a deep red to lighter orange-red skin color, and a flesh color which is golden yellow; the fruit of the subject variety having an excellent flavor, and noteworthy aroma.

* * * * *

U.S. Patent Apr. 25, 1989 Plant 6,759
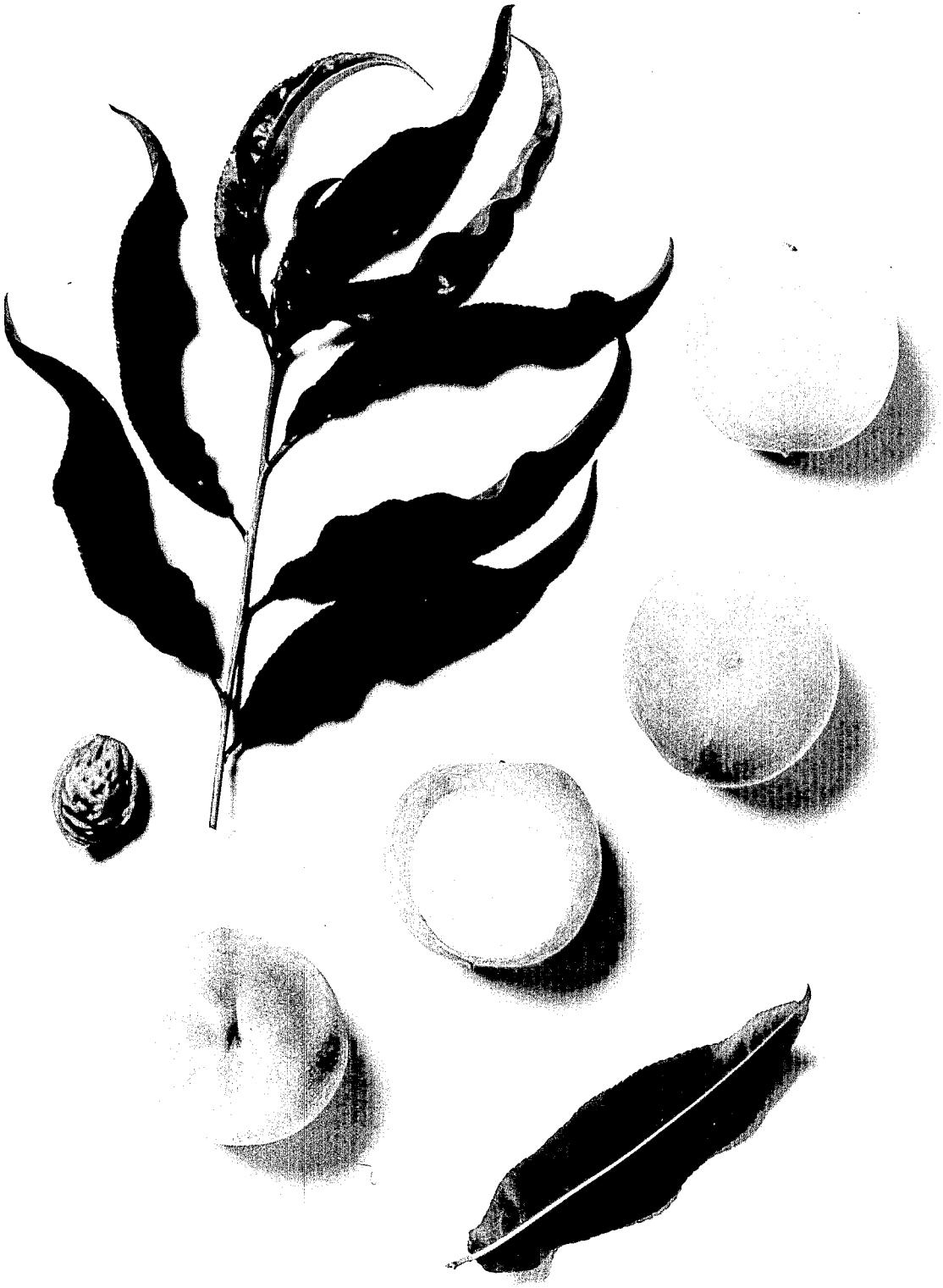

UNITED STATES PATENT AND TRADEMARK OFFICE

CERTIFICATE OF CORRECTION

PATENT NO. : Plant 6,759

DATED : April 25, 1989

INVENTOR(S) : James F. Doyle

It is certified that error appears in the above-identified patent and that said Letters Patent is hereby corrected as shown below:

Column 3, line 34, delete "17H-5" and substitute ---17-G-5---.

Column 3, line 46, delete "surfaces" and substitute ---surface---.

Column 3, line 52, delete ")" and substitute ---(--- before "19".

Column 3, line 53, delete "(i".

Column 4, line 35, delete "17-(-4" and substitute ---17-I-4---.

Column 4, line 40, delete "4-JH-11" and substitute ---4-J-11---.

Column 6, line 1, delete "p0".

Signed and Sealed this

Fifth Day of December, 1989

*Attest:*

JEFFREY M. SAMUELS

*Attesting Officer*

*Acting Commissioner of Patents and Trademarks*